United States Patent
Park et al.

(10) Patent No.: US 12,388,169 B2
(45) Date of Patent: Aug. 12, 2025

(54) ELECTRONIC DEVICE INCLUDING ANTENNA AND METHOD THEREFOR

(71) Applicant: SAMSUNG ELECTRONICS CO., LTD., Suwon-si (KR)

(72) Inventors: Chungsoon Park, Suwon-si (KR); Youngjae Ko, Suwon-si (KR); Kijung Kim, Suwon-si (KR); Junghyun Kang, Suwon-si (KR); Hyohoon Shin, Suwon-si (KR); Yongsang Yun, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 215 days.

(21) Appl. No.: 18/224,906

(22) Filed: Jul. 21, 2023

(65) Prior Publication Data

US 2023/0361453 A1    Nov. 9, 2023

Related U.S. Application Data

(63) Continuation of application No. PCT/KR2022/003127, filed on Mar. 4, 2022.

(30) Foreign Application Priority Data

Mar. 22, 2021    (KR) ........................ 10-2021-0036884

(51) Int. Cl.
*H01Q 1/27*    (2006.01)
*A61B 5/00*    (2006.01)
*H01Q 1/52*    (2006.01)

(52) U.S. Cl.
CPC .............. *H01Q 1/273* (2013.01); *H01Q 1/52* (2013.01); *A61B 5/681* (2013.01)

(58) Field of Classification Search
CPC .......... H01Q 1/273; H01Q 1/52; H01Q 1/243; A61B 5/681
See application file for complete search history.

(56) References Cited

U.S. PATENT DOCUMENTS 9,728,854 B2    8/2017   Kim et al.
10,020,572 B2   7/2018   Kim et al.
(Continued)

FOREIGN PATENT DOCUMENTS

CN    211480282 U    9/2020
JP    2000-056045 A  2/2000
(Continued)

OTHER PUBLICATIONS

Communication issued on Jun. 24, 2024 by the European Patent Office for European Patent Application No. 22775943.8.
(Continued)

*Primary Examiner* — Dieu Hien T Duong
(74) *Attorney, Agent, or Firm* — Sughrue Mion, PLLC

(57)    ABSTRACT

An electronic device includes: a conductive housing; a main circuit board; and a biometric circuit board configured to measure body information, wherein the biometric circuit board may include: a first connection point at which a first conductive connection member contacts the biometric circuit board, the first conductive connection member being configured to electrically connect the conductive housing and the biometric circuit board; a second connection point at which a second conductive connection member contacts the biometric circuit board, the second conductive connection member being configured to electrically connect a biometric button and the biometric circuit board; and a third connection point at which a third conductive connection member contacts the biometric circuit board, the third conductive connection member being configured to electrically connect the main circuit board and the biometric circuit board, and (Continued)

the conductive housing may include a first shorting point electrically connected to the biometric circuit board and the main circuit board to provide an antenna path.

15 Claims, 10 Drawing Sheets

(56) References Cited

U.S. PATENT DOCUMENTS

| | | | |
|---|---|---|---|
| 10,116,346 B2 | 10/2018 | Kim et al. | |
| 10,236,560 B2 | 3/2019 | Shin et al. | |
| 10,250,064 B2 | 4/2019 | Park et al. | |
| 10,420,483 B2 | 9/2019 | Lee et al. | |
| 10,608,323 B2 | 3/2020 | Choi et al. | |
| 10,682,094 B2 | 6/2020 | Kim et al. | |
| 10,700,416 B2 | 6/2020 | Jung et al. | |
| 11,271,304 B2 | 3/2022 | Yoo et al. | |
| 2016/0064820 A1 | 3/2016 | Kim et al. | |
| 2017/0168462 A1 | 6/2017 | Ryu et al. | |
| 2017/0296088 A1 | 10/2017 | Choi | |
| 2018/0228370 A1 | 8/2018 | Wang et al. | |
| 2018/0293420 A1* | 10/2018 | Kim | H05K 1/189 |
| 2020/0153084 A1 | 5/2020 | Yun | |
| 2020/0194905 A1 | 6/2020 | Wei et al. | |
| 2020/0312460 A1 | 10/2020 | Lee et al. | |
| 2020/0365974 A1 | 11/2020 | Wei et al. | |
| 2021/0057819 A1 | 2/2021 | Yoo et al. | |

FOREIGN PATENT DOCUMENTS

| | | |
|---|---|---|
| KR | 10-2011-0131750 A | 12/2011 |
| KR | 10-2015-0119748 A | 10/2015 |
| KR | 10-2016-0027700 A | 3/2016 |
| KR | 10-2016-0036426 A | 4/2016 |
| KR | 10-2017-0020138 A | 2/2017 |
| KR | 10-2017-0071267 A | 6/2017 |
| KR | 10-2017-0072700 A | 6/2017 |
| KR | 10-2017-0118439 A | 10/2017 |
| KR | 10-2018-0026861 A | 3/2018 |
| KR | 10-2018-0039425 A | 4/2018 |
| KR | 10-1964651 B1 | 4/2019 |
| KR | 10-2019-0067872 A | 6/2019 |
| KR | 10-2019-0092097 A | 8/2019 |
| KR | 10-2020-0113550 A | 10/2020 |

OTHER PUBLICATIONS

International Search Report & Written Opinion (PCT/ISA/210 & 237) issued Jun. 13, 2022 from the International Searching Authority in International Application No. PCT/KR2022/003127.

* cited by examiner

ELECTRONIC DEVICE INCLUDING ANTENNA AND METHOD THEREFOR

CROSS-REFERENCE TO RELATED APPLICATIONS

This application is a by-pass continuation application of International Application No. PCT/KR2022/003127, filed on Mar. 4, 2022, which is based on and claims priority to Korean Patent Application No. 10-2021-0036884, filed on Mar. 22, 2021, in the Korean Intellectual Property Office, the disclosures of which are incorporated by reference herein their entireties.

BACKGROUND

1. Field

The disclosure relates to an electronic device, and more particularly, to an electronic device including an antenna and a method thereof.

2. Description of Related Art

An antenna may form a loop through a shorting point between a metal housing and a main board. The loop may vary based on a position of the shorting point; thus, a length of the antenna may vary.

In related art, the number of shorting points for adjusting a length of the antenna may be limited by an area of an internal structure of an electronic device. More antenna space may be needed to implement more shorting points. However, this may not be appropriate for the current trend of miniaturization of electronic devices.

SUMMARY

According to an aspect of the disclosure, an electronic device may include: a conductive housing; a main circuit board; and a biometric circuit board configured to measure body information, wherein the biometric circuit board may include: a first connection point at which a first conductive connection member contacts the biometric circuit board, the first conductive connection member being configured to electrically connect the conductive housing and the biometric circuit board; a second connection point at which a second conductive connection member contacts the biometric circuit board, the second conductive connection member being configured to electrically connect a biometric button and the biometric circuit board; and a third connection point at which a third conductive connection member contacts the biometric circuit board, the third conductive connection member being configured to electrically connect the main circuit board and the biometric circuit board, and the conductive housing may include a first shorting point electrically connected to the biometric circuit board and the main circuit board to provide an antenna path.

The biometric button may be provided at a surface of the conductive housing and electrically isolated from the conductive housing.

The first shorting point may be provided at the conductive housing and the first shorting point may be connected to the first connection point through the first conductive connection member.

The biometric circuit board may be connected to the biometric button of the conductive housing to transmit or receive biometric information and biometric button signals.

The biometric circuit board further may include a first capacitor configured to block biosignal interference between the first connection point and the third connection point.

The biometric circuit board further may include a first inductor configured to block radio frequency (RF) signal interference between the second connection point and the third connection point.

The main circuit board may include: an antenna circuit configured to transmit or receive a radio frequency (RF) signal; a biometric sensor configured to transmit or receive a biosignal; and a fourth connection point connected to the third connection point through the third conductive connection member, and provided between the antenna circuit and the biometric sensor.

The main circuit board further may include a second capacitor configured to block biosignal interference between the fourth connection point and the antenna circuit.

The main circuit board may further include a second inductor configured to block RF signal interference between the fourth connection point and the biometric sensor.

The biometric circuit board may include a flexible printed circuit board, and each of the first, second, and third conductive connection members may include a c-clip.

The electronic device may further include: a feeding point; a second shorting point generated through a contact between the conductive housing and the main circuit board; and a processor configured to control whether an antenna is used and whether a radio frequency (RF) signal is transmitted or received.

In the antenna, a high resonant frequency may move to a high band as a distance between the feeding point and the second shorting point decreases, and a low resonant frequency may move to a lower band as a distance between the feeding point and the second shorting point increases.

The electronic device may further include a first switch, the first switch may be switched to connect the feeding point and the first shorting point or the first switch may be switched to connect the feeding point and the second shorting point, and the processor may be further configured to control a switching of a path of the RF signal of the first switch.

Based on the feeding point and the first shorting point that are switched to be connected, a first resonant frequency of the antenna may be determined based on a distance between the feeding point and the first shorting point, and based on the feeding point and the second shorting point that are switched to be connected, a second resonant frequency of the antenna may be determined based on a distance between the feeding point and the second shorting point.

The electronic device may further include: a processor; an antenna circuit; a biometric sensor; a first switch; and a bioswitch, the processor may be configured to control a transmission or a reception of a radio frequency (RF) signal through the first switch connected to the antenna circuit, and the biometric sensor may be configured to control a transmission or a reception of a biosignal through the bioswitch.

According to one or more embodiments, by adding a contact point or a connection point with a metal housing to a biometric function application structure of an electronic device, a shorting point between an antenna and a main board can be increased through less space utilization.

According to one or more embodiments, by variously adjusting a length of the antenna through the added shorting point, a performance of the antenna can be improved.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
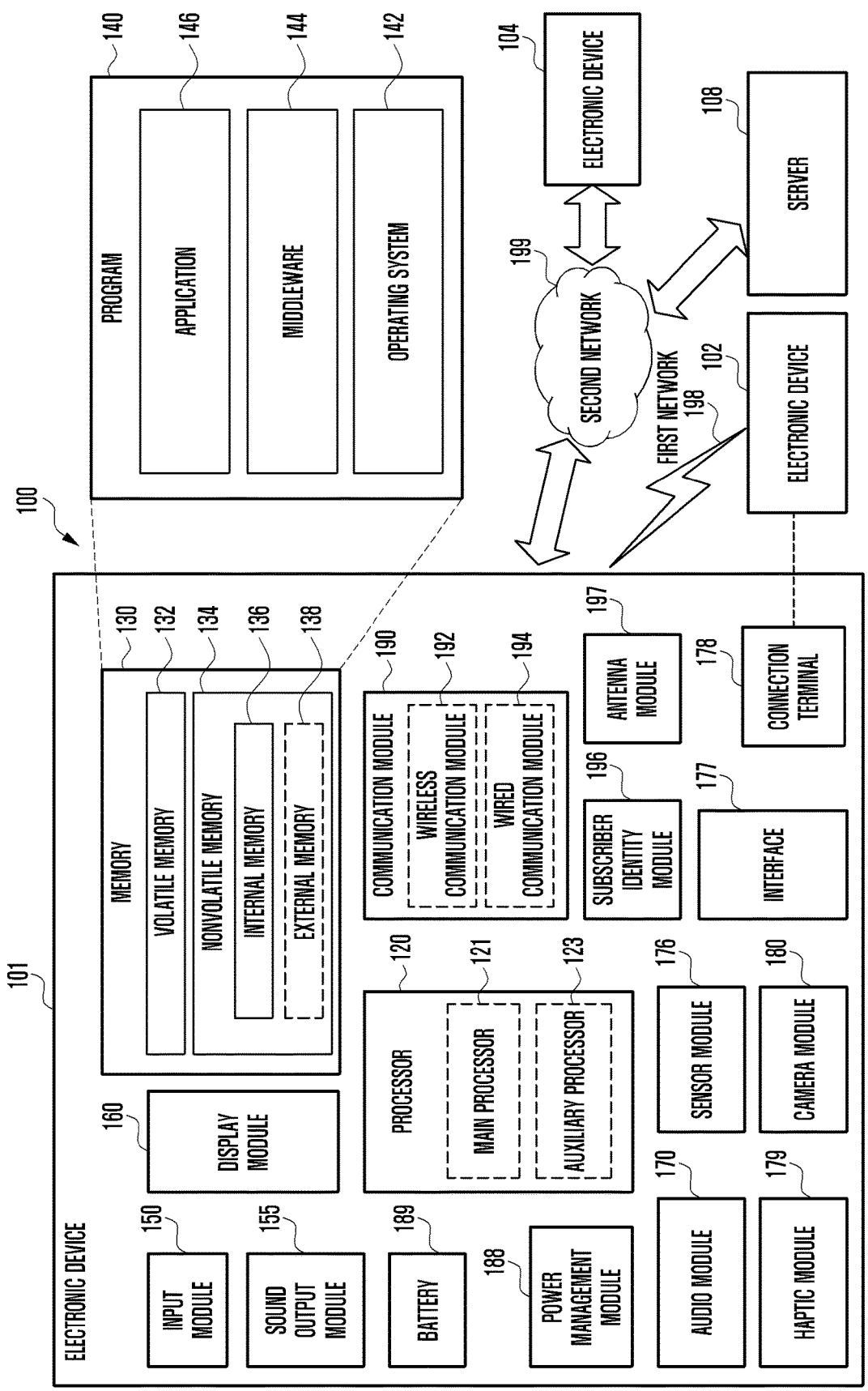
FIG. 1 is a block diagram illustrating an electronic device in a network environment according to one or more embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101.

The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
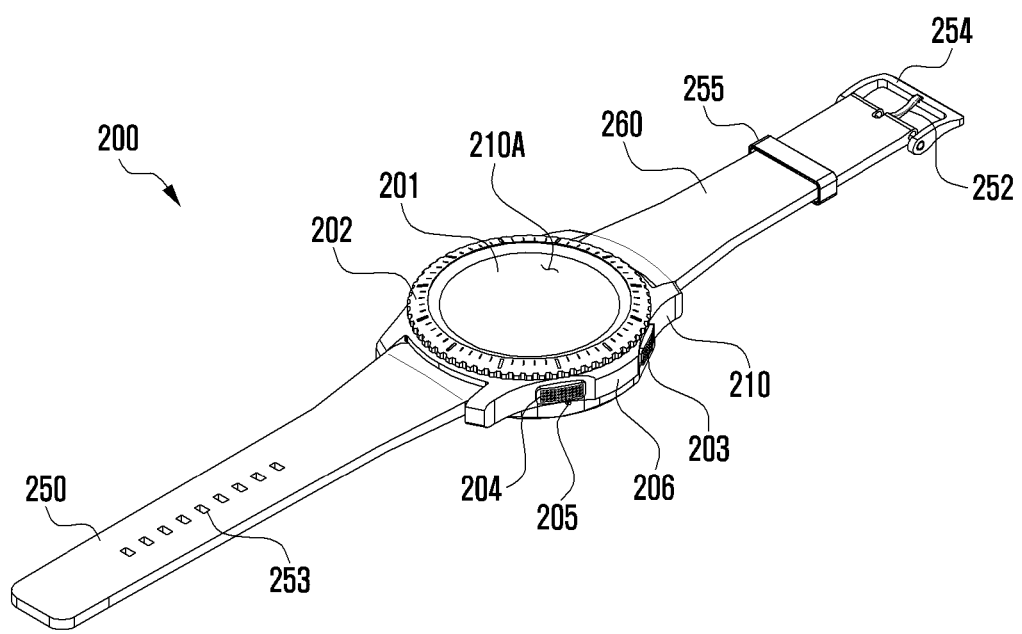
FIG. 2 is a perspective view illustrating a front surface of an electronic device according to one or more embodiments.
Figure 3:
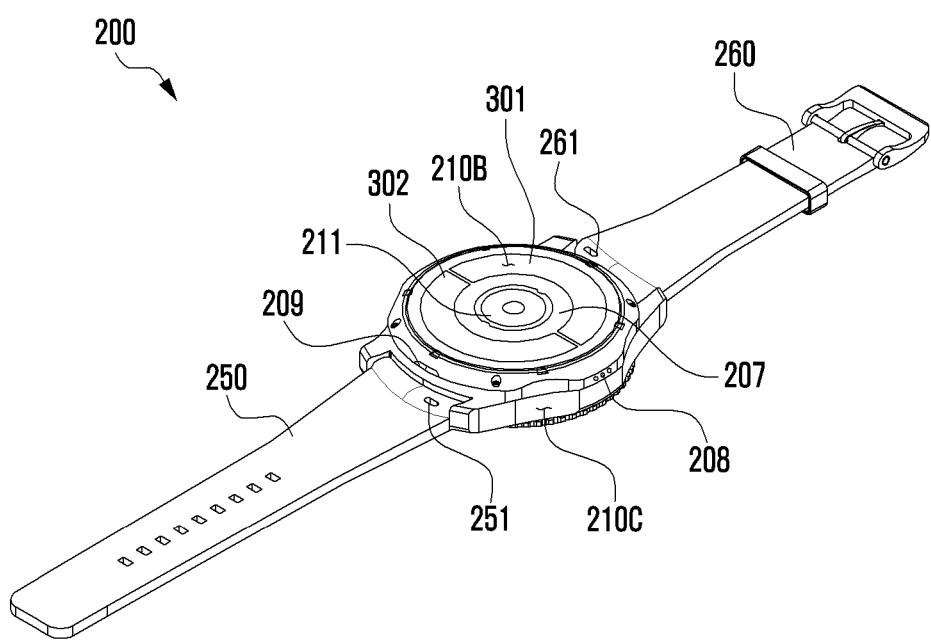
FIG. 3 is a perspective view illustrating a back surface of an electronic device according to one or more embodiments.

FIG. 2 is a perspective view illustrating a front surface of an electronic device according to one or more embodiments. FIG. 3 is a perspective view illustrating a back surface of the electronic device of FIG. 2.

An electronic device 200 illustrated in FIGS. 2 and 3 may be one of the electronic devices 101 described with reference to FIG. 1. Therefore, even if not described below, the electronic device 200 may include the components described with reference to FIG. 1.

With reference to FIGS. 2 and 3, the electronic device 200 according to an embodiment may include a housing 210 including a first surface (or front surface) 210A, a second surface (or back surface) 210B, and a side surface 210C enclosing a space between the first surface 210A and the second surface 210B, and fastening members 250 and 260 connected to at least a portion of the housing 210 and to detachably fasten the electronic device 200 to a user's body part (e.g., wrist, ankle, and the like). In another embodiment, the housing may refer to a structure forming some of the first surface 210A, the second surface 210B, and the side surface 210C of FIGS. 2 and 3. According to an embodiment, the first surface 210A may be formed by a front plate 201 (e.g., a glass plate or a polymer plate including various coating layers) at least partially substantially transparent. The second surface 210B may be formed by a substantially opaque back plate 207. The back plate 207 may be made of, for example, coated or tinted glass, ceramic, polymer, metal (e.g., aluminum, stainless steel (STS), or magnesium), or a combination of at least two of the above materials. The side surface 210C may be coupled to the front plate 201 and the back plate 207 and be formed by a side bezel structure (or "side member") 206 including metal and/or polymer. In some embodiments, the back plate 207 and the side bezel structure 206 may be integrally formed and include the same material (e.g., a metal material such as aluminum). The fastening members 250 and 260 may be formed with various materials and shapes. Integral and plurality of unit links may be formed to move with each other by woven material, leather, rubber, urethane, metal, ceramic, or a combination of at least two of the above materials.

According to an embodiment, the electronic device 200 may include at least one of a display 210a, audio modules 205 and 208, a sensor module 211, key input devices 202, 203 and 204, or a connector hole 209. In some embodiments, the electronic device 101 may omit at least one (e.g., the key input devices 202, 203, and 204, the connector hole 209, or the sensor module 211) of the components or may additionally include other components.

In an embodiment, the display 210a may be exposed through a significant portion of the front plate 201. A shape of the display 210a may be a shape corresponding to that of the front plate 201 and be various shapes such as a circular shape, an elliptical shape, or a polygonal shape. The display 210a may be coupled to or disposed adjacent to a touch detection circuit, a pressure sensor capable of measuring the intensity (pressure) of a touch, and/or a fingerprint sensor.

In an embodiment, the audio modules 205 and 208 may include a microphone hole 205 and a speaker hole 208. A microphone for acquiring external sound may be disposed inside the microphone hole 205, and in some embodiments, a plurality of microphones may be disposed to detect a direction of sound. The speaker hole 208 may be used as an external speaker and a receiver for a call. In some embodiments, the speaker hole 208 and the microphone hole 205 may be implemented into one hole, or a speaker may be included without the speaker hole 208 (e.g., piezo speaker).

In an embodiment, the electronic device 200 may support various frequency bands. For example, the electronic device 200 may support a cellular wireless communication (e.g., 2G, 3G, 4G, 5G) frequency band (e.g., 800 MHz to 2.8 GHz), a GPS communication frequency band (e.g., 1.2 GHz to 1.5 GHz), and/or a short-range wireless communication (e.g., WiFi, NFC, Bluetooth) frequency band (e.g., 2.4 GHz to 5 GHz). The electronic device 200 may include at least one antenna for supporting various frequency bands.

In an embodiment, the sensor module 211 may generate an electrical signal or data value corresponding to an internal operating state of the electronic device 200 or an external environmental state. The sensor module 211 may include, for example, a biometric sensor module 211 (e.g., HRM sensor) disposed at the second surface 210B of the housing 210. The electronic device 200 may further include a sensor module, for example, at least one of a gesture sensor, a gyro sensor, a barometric pressure sensor, a magnetic sensor, an acceleration sensor, a grip sensor, a color sensor, an infrared (IR) sensor, a biometric sensor, a temperature sensor, a humidity sensor, or an illuminance sensor.

The outer housing 210 of the electronic device 201 according to one or more embodiments may include a side surface enclosing at least a portion between the front cover and back plate 207. The side surface may include at least one key input device (e.g., 203, 204). For example, at least one key input device may include at least one side key button, a crown, and/or a biosignal key button. The biosignal key button may be, for example, a dummy key that is not be pushed, but it is not limited thereto. The biosignal key button may form a part (e.g., exposure surface) of a biosignal sensor (e.g., biometric sensor). For example, the biosignal key button may be coupled to the side surface of the outer housing 210 as a separate module or may be integrally included in the side surface of the outer housing 210. The biosignal key button may include at least one electrode for receiving a user's biometric information. The electronic device 201 may determine biometric information (e.g., electrocardiogram signal, heart rate signal, bioelectric impedance analysis (bio) information and skin response (galvanic skin response) information) of the user based on the signal acquired through the biosignal key button. In some embodiments, the biosignal key button is at least a part of the biometric sensor, but those skilled in the art will easily understand that a type of the biometric sensor is not limited thereto.

In an embodiment, the sensor module 211 may include electrodes (or electrode areas) 301 and 302 forming a part of the surface of the electronic device 200 and a biosignal detection circuit electrically (or operatively) connected to the electrodes 301 and 302. For example, the electrodes 301 and 302 may include a first electrode 301 and a second electrode 302 disposed at the second surface 210B of the housing 210. The sensor module 211 may be constituted such that the electrodes 301 and 302 may acquire an electrical signal from a part of the user's body and that the biosignal detection circuit detects the user's biometric information based on the electrical signal.

In an embodiment, the electronic device 200 may include a plurality of electrodes that may contact the user's body. The plurality of electrodes may include, for example, electrodes 301 and 302 disposed at the second surface 210B of the electronic device, as illustrated in FIG. 3, and an electrode disposed at the first surface 210A and/or the side surface 210C of the electronic device. A plurality of electrodes may be connected to each other as a circuit, but parts functioning as electrodes may be segmented from each other. For example, the electrodes may be composed of three electrodes including the electrodes 301 and 302 disposed at the second surface 210B and an electrode disposed at the side surface 210C. Various biometric information of the user may be detected through a plurality of electrodes. In an embodiment, information related to the user's electrocardiogram may be measured using a plurality of electrodes. Electrocardiogram measurement may be performed in various ways. For example, in the electrocardiogram measurement, the plurality of electrodes described above may include an INP (positive) electrode (e.g., electrode 301), an INM (negative) electrode, and a right-leg drive (RLD) electrode (e.g., electrode 302). Electrocardiogram measurement may be performed through the INP electrode and the RLD electrode. Here, the RLD electrode may be a connection point used for increasing an electrocardiogram measurement performance by reducing a signal having the same phase in an electrode that is in contact with the body.

In an embodiment, the key input devices 202, 203, and 204 may include a wheel key 202 disposed at the first surface 210A of the housing 210 and rotatable in at least one direction, and/or side key buttons 203 and 204 disposed at the side surface 210C of the housing 210. The wheel key 202 may have a shape corresponding to the shape of the front plate 201. In another embodiment, the electronic device 200 may not include some or all of the above-described key input devices 202, 203, and 204, and the key input devices 202, 203, and 204 that are not included may be implemented in other forms such as soft keys on the display 210a. The connector hole 209 may receive a connector (e.g., USB connector) for transmitting and receiving power and/or data to and from an external electronic device, and the electronic device 200 may include another connector hole that may receive a connector for transmitting and receiving an audio signal to and from an external electronic device. The electronic device 200 may further include, for example, a connector cover that covers at least a portion of the connector hole 209 and that blocks external foreign substances from entering the connector hole.

As another example, a separate window of the electronic device 201 may have a size substantially corresponding to a through hole of the housing 210 and be coupled (e.g., fitted) to the through hole of the housing 210. In this case, the display module 210a may be visually exposed (e.g., the first surface (display) 210a) through the through hole of the external housing 210. The window may be made of a transparent material. According to an embodiment, at least a partial surface (e.g., a surface exposed to the outside through a through hole) of the display module 210a may form the first surface (display) 210a of the electronic device 201.

For example, a shielding layer may provide a shielding function against electromagnetic waves generated in at least one electronic component (e.g., display driver IC (DDI) and display panel) included in or connected to the first surface (display) 210a. For example, a heat dissipation layer may provide a heat conduction function capable of reducing a heat generated by the electronic device 201 by transferring a heat generated in the at least one component to the outside. For example, the shielding layer and/or the heat dissipation layer may have a shape corresponding to a surface of a printed circuit board and/or at least one electronic component through a flat form (e.g., sheet, plate) or pre-forming. The shielding layer and the heat dissipation layer may be made of, for example, a steel use stainless (SUS) material, but it is not limited thereto. The shielding layer and the heat dissipation layer may be separately included or integrally included in the electronic device 101.

In an embodiment, the fastening members 250 and 260 may be detachably fastened to at least a partial area of the housing 210 using locking members 251 and 261. The fastening members 250 and 260 may include one or more of a fixing member 252, a fixing member fastening hole 253, a band guide member 254, and a band fixing ring 255.

In an embodiment, the fixing member 252 may fix the housing 210 and the fastening members 250 and 260 to a user's body part (e.g., wrist, ankle, and the like). The fixing member fastening hole 253 may fix the housing 210 and the fastening members 250 and 260 to a part of the user's body corresponding to the fixing member 252. The band guide member 254 may limit a movement range of the fixing member 252 when the fixing member 252 is fastened with the fixing member fastening hole 253; thus, the fastening members 250 and 260 may be attached to tightly contact a part of the user's body. The band fixing ring 255 may limit a movement range of the fastening members 250 and 260 in a state in which the fixing member 252 and the fixing member fastening hole 253 are fastened.

In an embodiment, the back plate 207 may be made of, for example, coated or tinted glass, ceramic, polymer, metal (e.g., aluminum, stainless steel (STS), or magnesium), or a combination of at least two of the above material.

Figure 4:
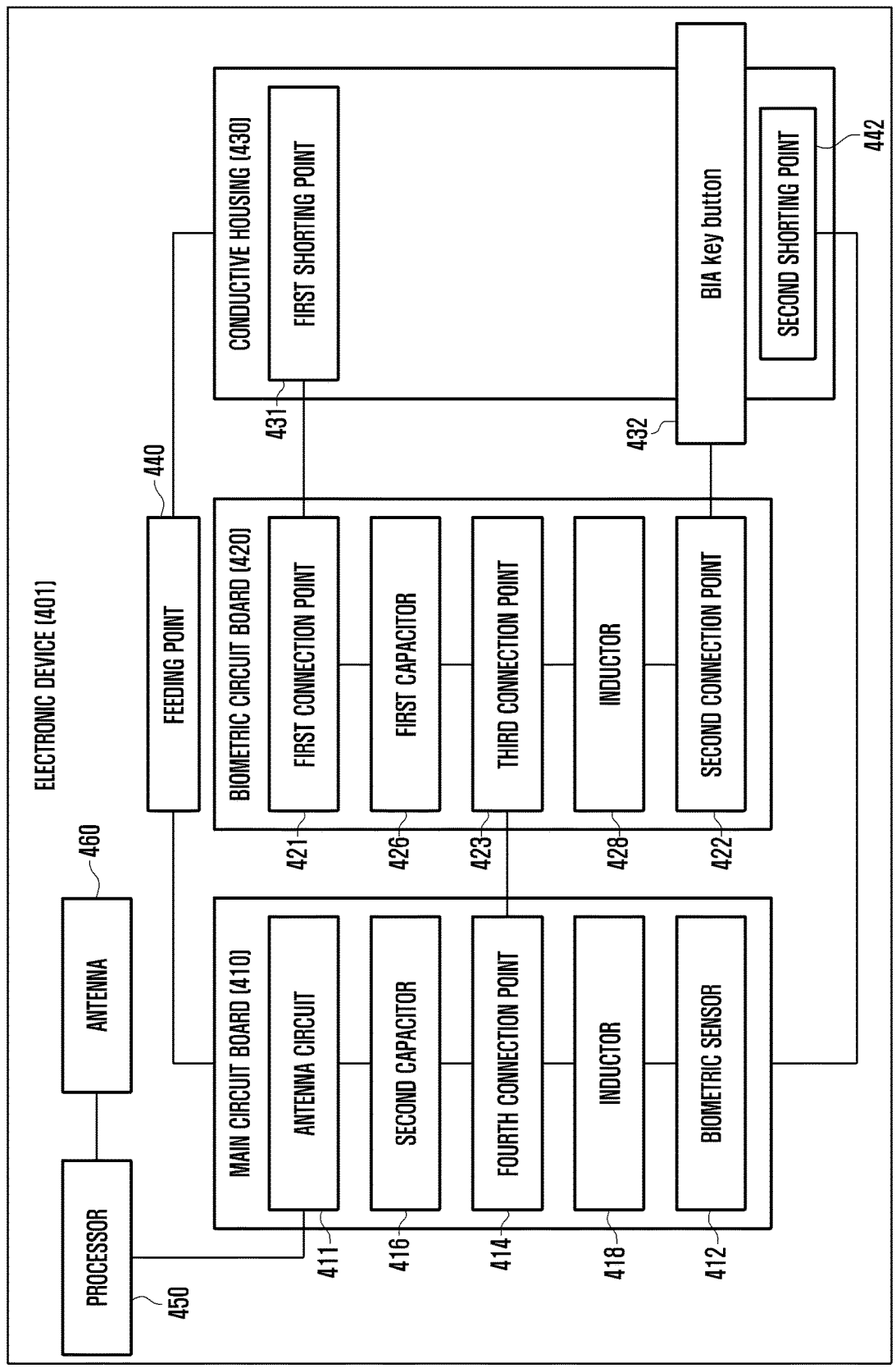
FIG. 4 is a block diagram illustrating a constitution of an electronic device according to one or more embodiments.

FIG. 4 is a block diagram illustrating a constitution of an electronic device according to one or more embodiments.

According to one or more embodiments, an electronic device 401 may include a main circuit board 410, a biometric circuit board 420, a conductive housing 430, and a processor 450. Further, the electronic device 401 may further include a feeding point 440 and a second shorting point 442 generated through a contact between the conductive housing 430 and the main circuit board 410. The main circuit board 410 and the conductive housing 430 may contact each other to form two short points, which may correspond to the feeding point 440 and the second shorting point 442. In the antenna, a high resonant frequency may move to a higher band as a distance between the feeding point and the shorting point decreases, and the resonant frequency may move to a lower band as a distance between the feeding point and the shorting point increases. An embodiment for this will be described in detail with reference to FIG. 10.

According to one or more embodiments, a contact area between the main circuit board 410 and the conductive housing 430 may include one feeding point and a shorting point in a structure of the electronic device 401. In this case, it may be difficult to adjust a length of the antenna corresponding to an increase in the number of frequency bands (e.g., cellular wireless communication frequency bands and short-distance wireless communication frequency bands) supported by the electronic device 401. In the case that it is difficult to adjust the length of the antenna, it may be difficult to optimize a radiation performance for each band. In other words, shorting points between the main circuit board 410 and the conductive housing 430 may be further required to variously adjust the length of the antenna.

According to one or more embodiments, the electronic device 401 may add the biometric circuit board 420 to add a shorting point between the main circuit board 410 and the conductive housing 430. Hereinafter, an embodiment of such an electronic device 401 will be described in more detail.

According to one or more embodiments, the biometric circuit board 420 may be positioned between the conductive housing 430 and the main circuit board 410. The biometric circuit board 420 may form two contact points with the conductive housing 430, which may include a first connection point 421 and a second connection point 422. The biometric circuit board 420 may form one contact point with the main circuit board 410, which may include a third connection point 423. In summary, the biometric circuit board 420 may include a first connection point 421, a second connection point 422, and a third connection point 423.

According to one or more embodiments, the first connection point 421 of the biometric circuit board 420 may be connected to a first shorting point 431 of the conductive housing 430 through a first conductive connection member. The second connection point 422 of the biometric circuit board 420 may be connected to a biosignal key button 432 (e.g., BIA key button) through the conductive connection member. The biosignal key button 432 is an electrode component for measuring biosignals and has been described as an element including a key button that moves in the case that an external force is applied to the biosignal key button 432, but it is not limited thereto and may include various structures of electrodes for measuring biosignals.

For example, the biosignal key button 432 is positioned at the conductive housing 430, but may be electrically insulated from the conductive housing 430 and be electrically insulated from a high frequency band of the antenna signal. Further, a part of the biosignal key button 432 may be exposed to the outside of the conductive housing 430. The biosignal key button 432 may measure bio-resistance according to the user's body contact to generate a biosignal. The generated biosignal may be transmitted to the main circuit board 410 through a flexible printed circuit board (FPCB) of the biometric circuit board 420. The third connection point 423 of the biometric circuit board 420 may be connected to a fourth connection point 414 of the main circuit board 410 through the conductive connection member. For example, the main circuit board 410 may form a contact point with the conductive housing 430 through the biometric circuit board, and in this case, the contact point may include a first shorting point 431.

According to an embodiment, the biometric circuit board 420 may further include a first capacitor 426 between the first connection point 421 and the third connection point 423. The first capacitor 426 may block interference between an RF signal of the first shorting point 431 transmitted to the first connection point 421 and a biosignal. Further, the biometric circuit board 420 may further include a first inductor 428 between the second connection point 422 and the third connection point 423. The first inductor 428 may block interference between an RF signal and a biosignal transmitted through the biosignal key button 432. For example, the biometric circuit board 420 may transmit the RF signal of the antenna and the biosignal to the main circuit board 410 through the first capacitor 426 and the first inductor 428 without mutual interference.

According to one or more embodiments, the main circuit board 410 may be physically or electrically connected to the conductive housing 430 through the fourth connection point 414. In an embodiment, the connection point may be formed by, for example, a C-clip, a conductive gasket, a metal (e.g., aluminum, stainless steel (STS), or magnesium), or a combination of at least two of the above materials.

An RF signal and/or biosignal path may be formed to the main circuit board 410 through the biometric circuit board 420. Further, conversely, an RF signal may be transmitted from an antenna circuit 411 to the biometric circuit board 420. A biosignal transmitted to the main circuit board 410 may be transmitted to a biometric sensor. Here, the biosignal may include a signal including user's biometric information or a user's biosignal. Further, conversely, an application signal for acquiring a biosignal may be transmitted from a biometric sensor 412 to the biometric circuit board 420. In this case, the RF signal and biosignal may be transmitted through the conductive connection member between the fourth connection point 414 and the third connection point 423. The main circuit board 410 may further include a second capacitor 416 between the antenna circuit 411 and the fourth connection point 414. The second capacitor 416 may block interference of biosignals or applied signals during RF signal transmission and/or reception. The main circuit board 410 may further include a second inductor 418 between the biometric sensor 412 and the fourth connection point 414. The second inductor 418 may block interference of RF signals during transmission and/or reception of biosignals or application signals. Mutual interference between signals may be prevented while transmitting a plurality of signals with one path through the second inductor 418 and the second capacitor 418.

According to one or more embodiments, the electronic device 401 may include a processor 450. The processor 450 is a component capable of performing calculations or data processing related to control and/or communication of each component of the electronic device 401, and may include one or more processors. The processor 450 may include at least some of the components and/or functions of the processor 120 of FIG. 1. Calculations and data processing functions that the processor 450 may implement in the electronic device will not be limited, but hereinafter, features related to control of the switching device will be described in detail. Operations of the processor 450 may be performed by loading instructions stored in a memory.

According to an embodiment, the processor 450 may control transmission and/or reception of an RF signal through a first switch connected to the antenna circuit 411. Further, the processor 450 may control a switching operation between the first shorting point 431 and the second shorting point 442. The loop structure of the antenna may be changed according to the switching operation of the processor 450, and the length of the antenna may be changed according to the change of the loop structure. In the case that the length of the antenna is changed, the resonant frequency of the antenna may also be changed. An embodiment related to the change of the resonant frequency of the antenna according to the control of the switching operation of the processor 450 will be described with reference to FIG. 10.

According to an embodiment, the electronic device 401 may provide bioelectric impedance analysis (BIA) information. Bioelectrical impedance analysis may be performed through the biometric sensor 412. The electronic device 401 may be worn on a user's body (e.g., wrist). In the case that the user wears the electronic device 401, the electrode, the heart rate sensor module, and the temperature sensor may contact or come close to the user's body. In this case, in order to provide information on the user's health status, the electronic device 401 may measure the user's biosignal through at least one sensor and/or at least one electrode (e.g., an electrode included in a biometric key button). For example, the electronic device 401 may measure the user's body temperature through a temperature sensor. Further, the electronic device 401 may measure a biosignal (e.g., galvanic skin response (GSR)) for stress and emotion analysis through two electrodes. Further, the electronic device 401 may constantly measure a heart rate, measure changes in blood pressure, and measure blood flow through the heart rate sensor module. Further, the electronic device 401 may measure outdoor visibility (illuminance) and blue light through an RGB sensor. Further, the electronic device 401 may measure ultraviolet rays through the heartbeat sensor module.

According to an embodiment, in the case that a user close touches the heart rate sensor module with a finger of a hand not wearing the electronic device 401, the electronic device 401 may measure a heart rate and oxygen saturation (saturation pulse oximetry O2 (SPO2)) through the heart rate sensor module. Further, in the case that the user touches one of the electrodes with a hand not wearing the electronic device 401, the electronic device 401 may provide electrocardiogram information based on a biosignal measured through one of the electrodes. Further, in the case that the user touches both electrodes with a hand not wearing the electronic device 401, the electronic device 401 may provide bioelectrical impedance information based on a biosignal measured through two electrodes. Bio-resistance analysis indicates the degree of tissue hydration and an amount of body fluid, and may enable to know a body composition, fluid balance, and cell health. For example, the electronic device 401 may provide nutritional therapy related to biological age, detoxification state, obesity level, total amount of water in the body, prognosis of critically ill patients (e.g., cancer, renal dialysis patients), early check for lymphedema, and metabolic diseases (e.g., diabetes, hypertension, stroke, arteriosclerosis) through biometric measurement. Further, in the case that the user close touches one of the electrodes and the heart rate sensor module with a hand not wearing the electronic device 401, the electronic device 401 may provide blood pressure information based on the measured biosignal.

According to an embodiment, the electronic device 401 may constantly measure at least one of stress, emotion change, heart rate, blood pressure change, or blood flow through the electrode and the heart rate sensor module, and measure at least one of electrocardiogram, bio-resistance analysis, blood pressure, or oxygen saturation, if necessary.

Figure 5:
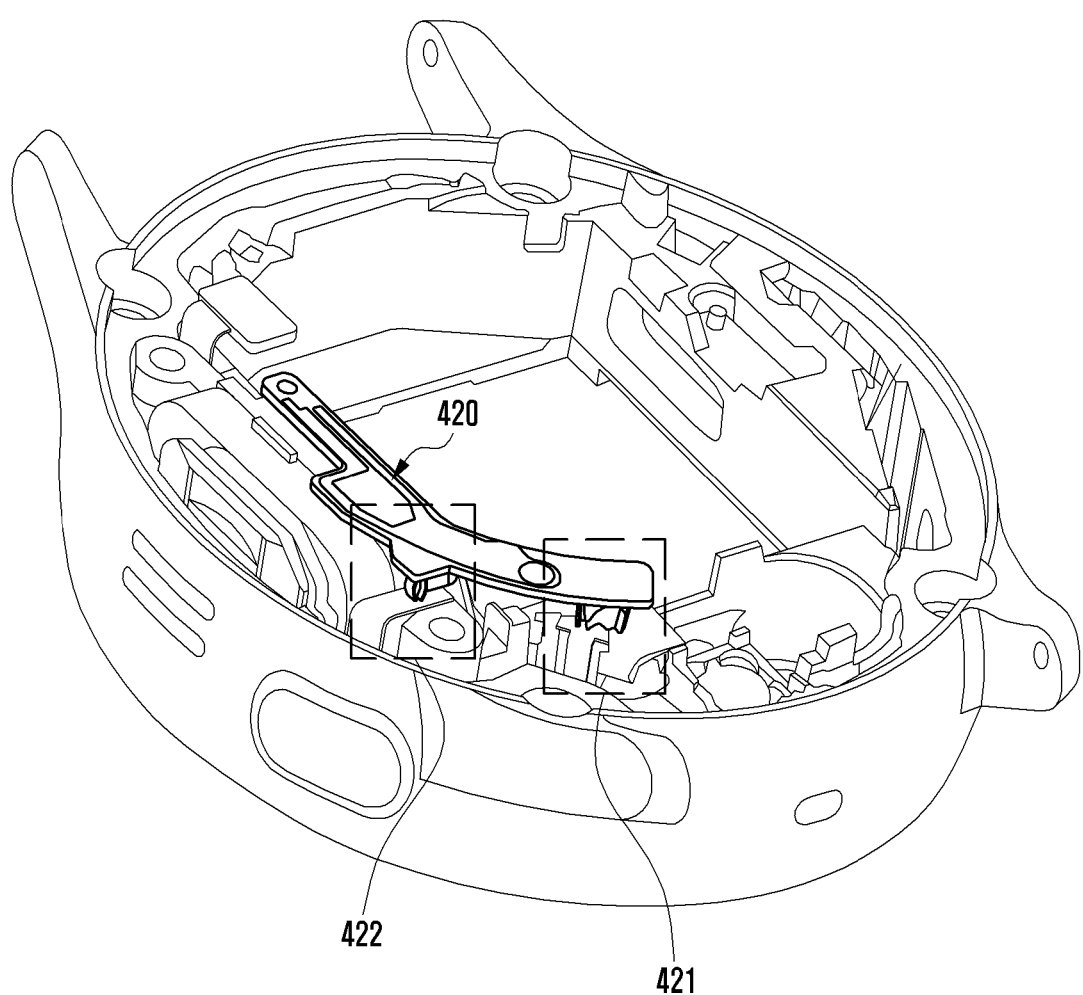
FIGS. 5 and 6 illustrate an internal structure of an electronic device according to one or more embodiments.
Figure 6:
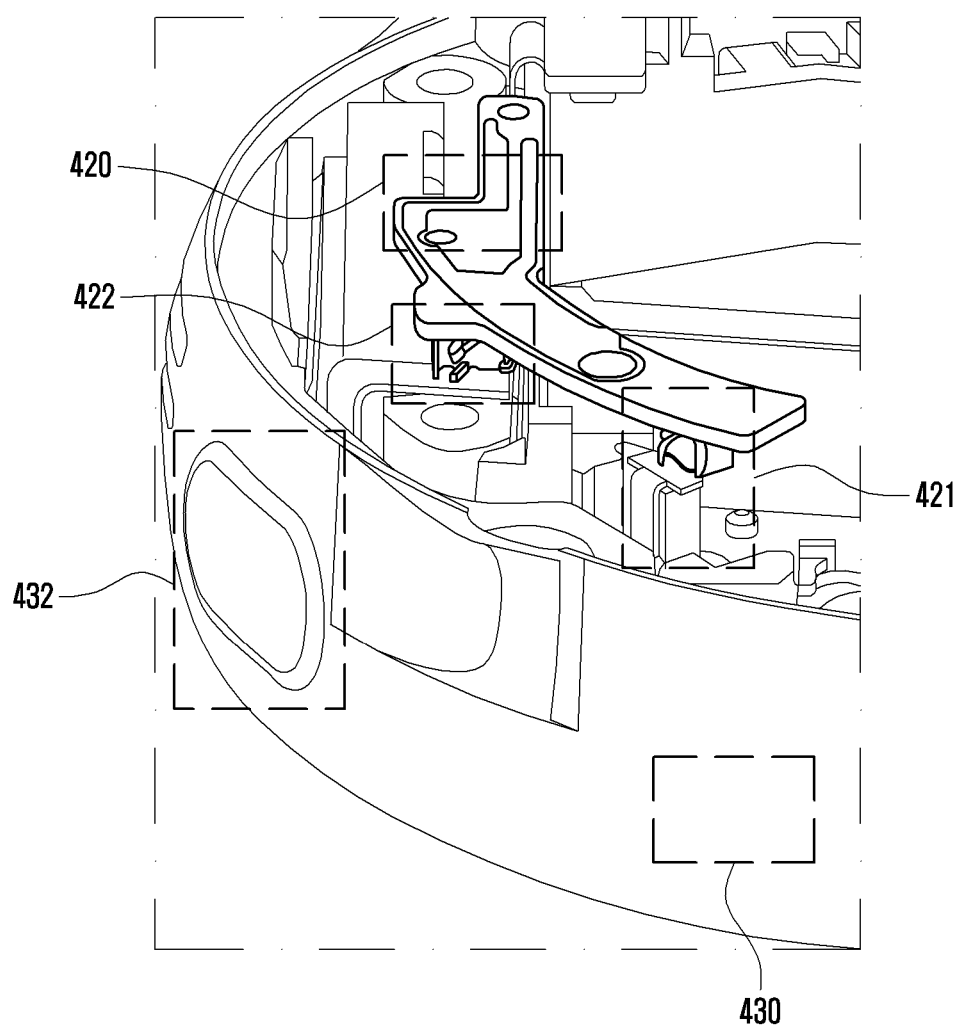

FIGS. 5 and 6 illustrate an internal structure of an electronic device according to one or more embodiments.

With reference to FIG. 5, the biometric circuit board 420 may have a conductive housing (e.g., the conductive housing 430 of FIG. 4) and two contact points (e.g., the first shorting point 431 and the second shorting point 442 of FIG. 4). One contact point is the first shorting point (e.g., the first shorting point 431 of FIG. 4) of the conductive housing (e.g., the conductive housing 430 of FIG. 4) and may be connected with the first connection point 421 of the biometric circuit board 420. Another contact point may include a biosignal key button (e.g., the biosignal key button 432 of FIG. 4) of the conductive housing 430, and be connected to the second connection point 422 of the biometric circuit board 420. However, although the biosignal key button 432 is physically disposed at the conductive housing 430, the biosignal key button 432 may maintain an electrically insulated state and maintain an electrically insulated state from a high frequency band of the antenna signal. For example, a point where the biometric circuit board 420 and the conductive housing 430 are electrically connected may correspond to only the first shorting point 431. In this case, the first shorting point 431 of the conductive housing 430 and the first connection point 421 of the biometric circuit board 420 may be connected through the conductive connection member. In this case, the conductive connection member may include a c-clip.

With reference to FIG. 6, a contact between the biometric circuit board (e.g., the biometric circuit board 420 of FIG. 4) and the conductive housing (e.g., the conductive housing 430 of FIG. 4) has been described in detail with reference to FIGS. 4 and 5. The second connection point (e.g., the second connection point 422 of FIG. 4) of the biometric circuit board 420 may be connected to the biosignal key button (e.g., a biosignal key button 432 of FIG. 4) through the conductive connection member. However, although the biosignal key button 432 is positioned at the conductive housing 430, the biosignal key button 432 may be electrically insulated from the conductive housing 430 or may be electrically insulated from the high frequency band of the antenna signal, as described above with reference to FIG. 5. For example, the main circuit board 410 may form a shorting point (e.g., the first shorting point 431 of FIG. 4) with the conductive housing 430 through the biometric circuit board 420. The shorting point may be used as a path of an antenna signal. The first shorting point 431 of the biosignal key button 432 may be positioned at the conductive housing 430 and be connected to the first connection point 421 through the conductive connection member. An embodiment of a case of newly forming a shorting point will be described with reference to FIG. 10.

Figure 7:
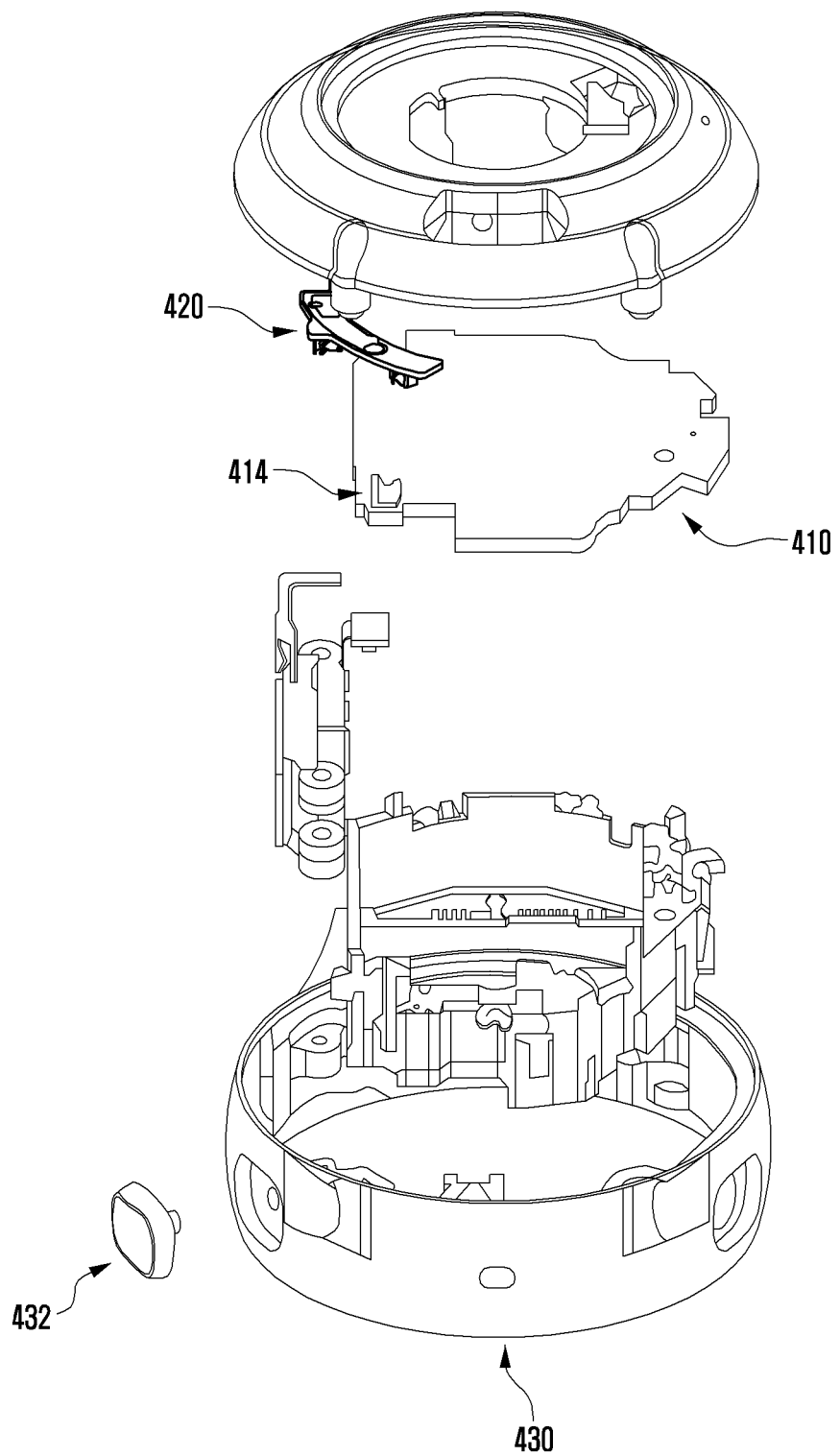
FIGS. 7 and 8 are exploded views illustrating an internal structure of an electronic device according to one or more embodiments.
Figure 8:
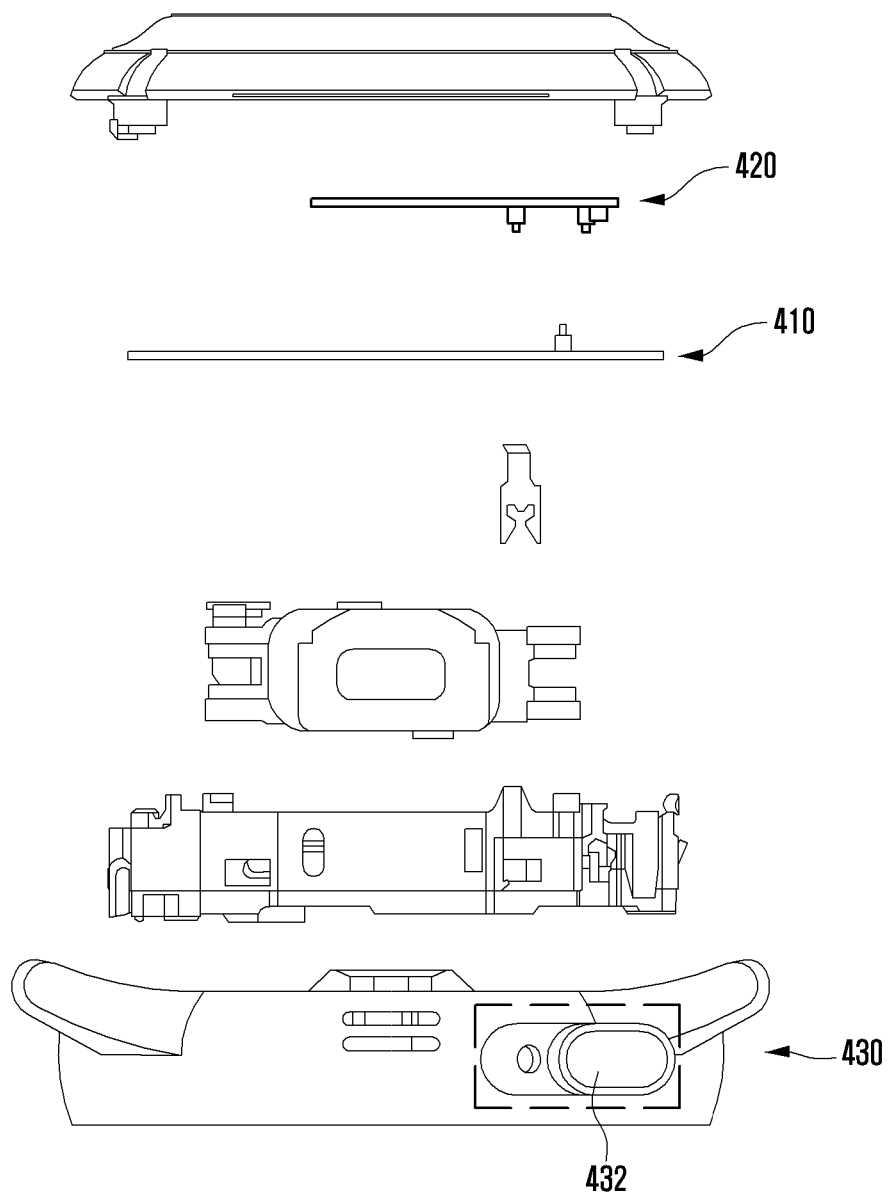

FIGS. 7 and 8 are exploded views illustrating an internal structure of an electronic device according to one or more embodiments.

With reference to FIGS. 7 and 8, an electronic device (e.g., the electronic device 401 of FIG. 4) may include a conductive housing 430 and a biosignal key button 432 at the outside. The main circuit board 410 may be disposed inside the conductive housing 430. The biometric circuit board 420 may be disposed between the conductive housing 430 and the main circuit board 410. The biometric circuit board 420 may form a connection point with the conductive housing 430 and the main circuit board 410, which has been previously described with reference to FIG. 4.

According to an embodiment, the biometric circuit board 420 may include a first connection point (e.g., the first connection point 421 of FIG. 4), a second connection point (e.g., the second connection point 422 of FIG. 4), and a third connection point (e.g., the third connection point 423 of FIG. 4). The biometric circuit board 420 may further include a first capacitor (e.g., the first capacitor 426 of FIG. 4) for blocking biosignal interference between the first connection point 421 and the third connection point 423. The biometric circuit board 420 may further include a first inductor (e.g., the first inductor 428 of FIG. 4) for blocking RF signal interference between the second connection point 422 and the third connection point 423.

According to an embodiment, the main circuit board 410 may further include a fourth connection point 414 connected to the biometric circuit board 420. The main circuit board 410 may further include an antenna circuit (e.g., the antenna circuit 411 of FIG. 4) and a biometric sensor (e.g., the biometric sensor 412 of FIG. 4). The main circuit board 410 may further include a second capacitor (e.g., the second capacitor 416 of FIG. 4) for blocking biosignal interference between the fourth connection point 414 and the antenna circuit 411. The main circuit board 410 may further include a second inductor (e.g., the second inductor 418 of FIG. 4) for blocking RF signal interference between the fourth connection point 414 and the biometric sensor 412.

According to an embodiment, the biometric circuit board 420 may include an FPCB, and the conductive connection member may include a c-clip.

Figure 9:
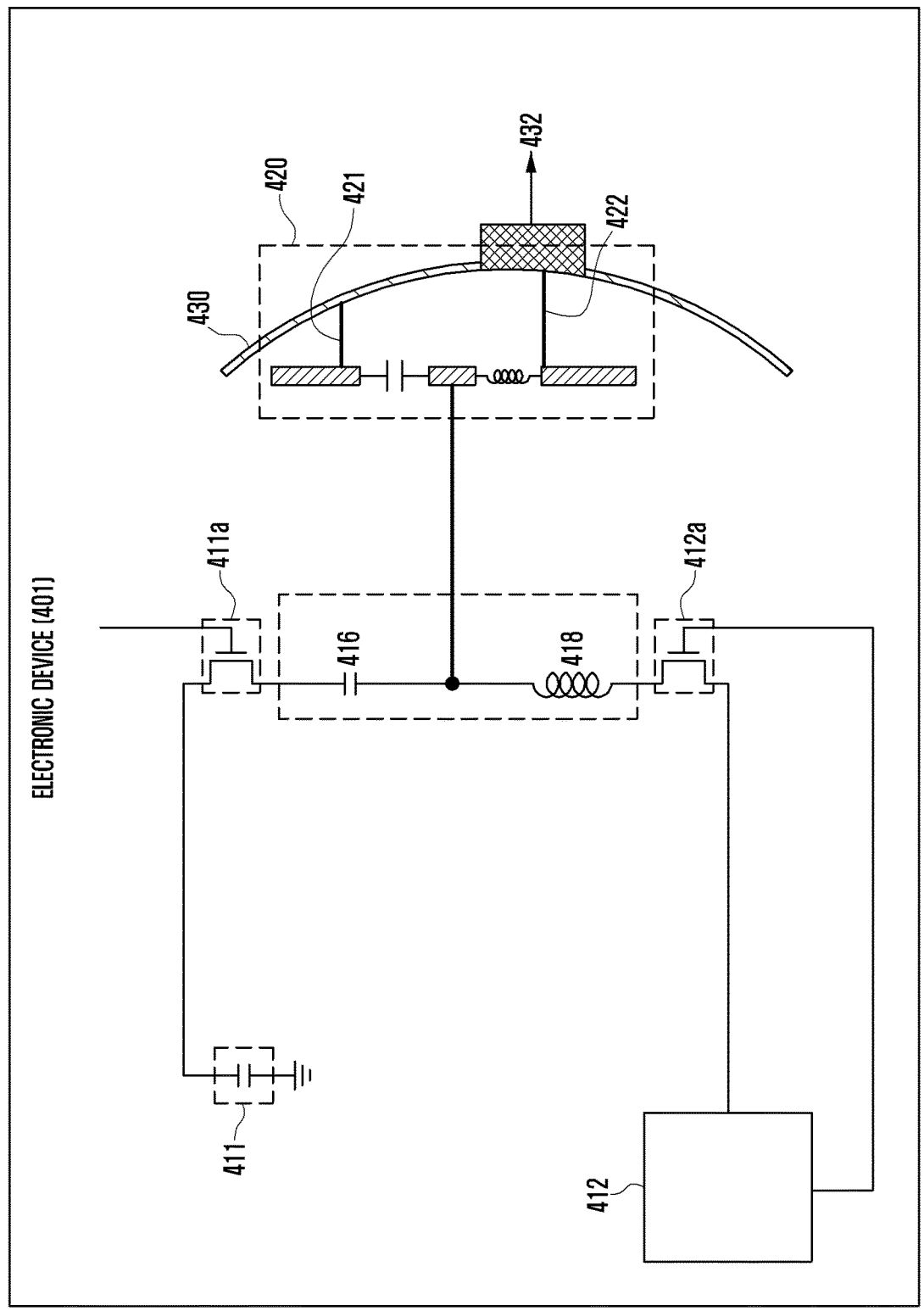
FIG. 9 is a top plan view illustrating an electronic device according to one or more embodiments.

FIG. 9 is a top plan view illustrating an electronic device according to one or more embodiments.

According to one or more embodiments, an electronic device (e.g., the electronic device 401 of FIG. 4) may include a main circuit board (e.g., the main circuit board 410 of FIG. 4), a biometric circuit board 420, and a conductive housing (e.g., the conductive housing 430 of FIG. 4). The biometric circuit board 420 may be positioned between the main circuit board 410 and the conductive housing 430. The biometric circuit board 420 may form two contact points (e.g., the first shorting point 431 and the biosignal key button 432 of FIG. 4) with the conductive housing 430. Although the biosignal key button 432 is disposed in the conductive housing 430, the biosignal key button 432 may be electrically insulated from the conductive housing 430 and be in a state electrically insulated from the high frequency band of the antenna signal. Therefore, an electrical connection point of the antenna signal between the biometric circuit board 420 and the conductive housing 430 may include only the first shorting point 431, except for the biosignal key button 432.

According to an embodiment, the biometric circuit board 420 may form one connection path with the main circuit board 410. The third connection point (e.g., the third connection point 423 of FIG. 4) of the biometric circuit board 420 and the fourth connection point (e.g., the fourth connection point 414 of FIG. 4) of the main circuit board 410 may form a connection path through the conductive connection member. A connection path between the main circuit board 410 and the conductive housing 430 may be formed through such a connection path and the connection path of the first shorting point 431 of the conductive housing 430. Through such a connection path, the main circuit board 410 and the conductive housing 430 may further form one shorting path. A resonant frequency of the antenna may be controlled through the shorting path, and an embodiment of this process will be described with reference to FIG. 10.

According to an embodiment, the biometric circuit board 420 may include a first connection point 421, a second connection point 422, and a third connection point 423. The biometric circuit board 420 may further include a first capacitor (e.g., the first capacitor 426 of FIG. 4) for blocking biosignal interference between the first connection point 421 and the third connection point 423. The biometric circuit board 420 may further include a first inductor (e.g., the first inductor 428 of FIG. 4) for blocking RF signal interference between the second connection point 422 and the third connection point 423.

According to an embodiment, the main circuit board 410 may further include a fourth connection point 414 connected to the biometric circuit board 420. The main circuit board 410 may further include an antenna circuit 411 and a biometric sensor 412. The main circuit board 410 may further include a first switch 411a for connecting the antenna circuit 411 and the fourth connection point 414. The main circuit board 410 may further include a second switch 412a for connecting the biometric sensor 412 and the fourth connection point 414.

According to an embodiment, the processor 450 may control to connect the antenna circuit 411 and the fourth connection point 414 through the first switch 411a. When the antenna circuit 411 and the fourth connection point 414 are connected, RF signals may be transmitted and/or received between the main circuit board 410 and the biometric circuit board 420. The processor 450 may control to connect the biometric sensor 412 and the fourth connection point 414 through the second switch 412a. When the biometric sensor 412 and the fourth connection point 414 are connected, biosignals may be transmitted and/or received between the main circuit board 410 and the biometric circuit board 420.

According to an embodiment, the main circuit board 410 may further include a second capacitor 416 for blocking biosignal interference between the fourth connection point 414 and the antenna circuit 411. The main circuit board 410 may further include a second inductor 418 for blocking RF signal interference between the fourth connection point 414 and the biometric sensor 412.

According to an embodiment, the electronic device 401 may further include a feeding point (e.g., the feeding point 440 of FIG. 4) and a second shorting point (e.g., the second shorting point 442 of FIG. 4) generated through a contact between the conductive housing 430 and the main circuit board 410. In the antenna, as a distance between the feeding point 440 and the second shorting point 442 decreases, a resonance position of the antenna may move to a higher band. Further, in the antenna, as a distance between the feeding point 440 and the second shorting point 442 increases, a resonance position of the antenna may move to a lower band. Hereinafter, in FIG. 10, an embodiment of adjusting the resonant distance and resonant frequency of the antenna will be described.

Figure 10:
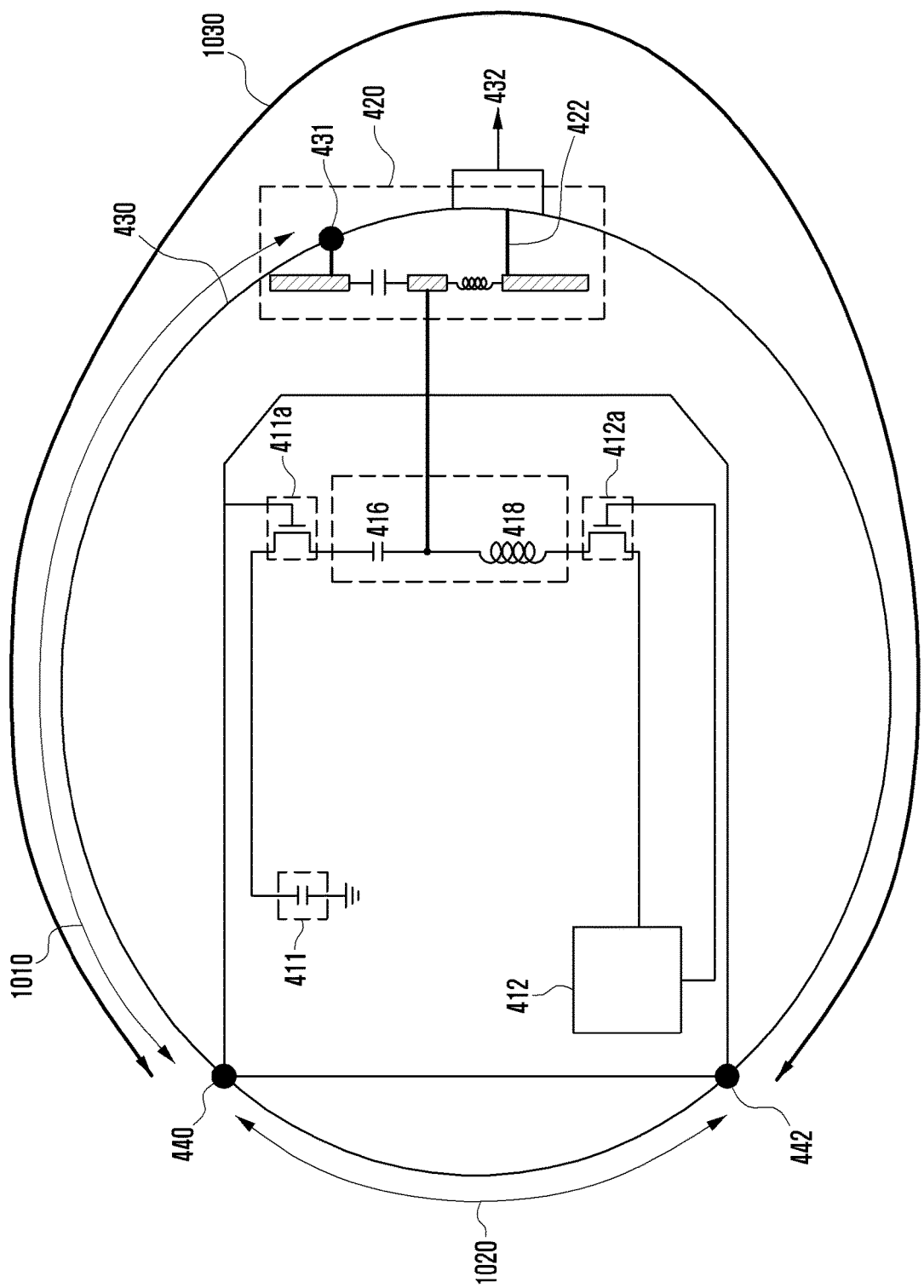
FIG. 10 illustrates three-dimensionally a shape in which a shorting point and a loop structure of an antenna are formed according to one or more embodiments.

FIG. 10 illustrates three-dimensionally formation of a loop structure of an antenna according to one or more embodiments.

According to an embodiment, the electronic device (e.g., the electronic device 401 of FIG. 4) may form a loop of the antenna through the feeding point 440 and the first shorting point 431 in addition to the feeding point 440 and the second shorting point 442, as described above with reference to FIGS. 4 to 9. As described above, the first shorting point 431 may include a shorting point newly formed in a process of adding a biometric sensor (e.g., the biometric sensor 412 of FIG. 4). A length of the antenna may vary according to a loop formation length, and a frequency of the antenna may vary according to the length of the antenna.

For example, in the case that an antenna loop is formed between the feeding point 440 and the second shorting point 442, the length of the antenna may be proportional to that of L2 1020 and/or L3 1030. In the case that an antenna loop is formed between the feeding point 440 and the first shorting point 431, the length of the antenna may be proportional to that of L1 1010. In this case, the length of L1 1010 may be longer than that of L2 1020, and the frequency of the antenna may move to a relatively low frequency band. The length of L1 1010 may be relatively shorter than that of L3 1030, and the frequency of the antenna may move to a relatively low frequency band. According to the addition of the biometric sensor 412, a shorting point may be added at no cost to variously make the frequency band of the antenna, thereby increasing a performance of the antenna.

According to one or more embodiments, an electronic device (e.g., the electronic device 401 of FIG. 4) may include a conductive housing (e.g., the conductive housing 430 of FIG. 4) including a body measurement area; a main circuit board (e.g., the electronic device 401 of FIG. 4); and a biometric circuit board (e.g., the biometric circuit board 420 of FIG. 4) configured to measure body information. The biometric circuit board 420 may include a first connection point (e.g., the first connection point 421 of FIG. 4), which is a point at which a first conductive connection member configured to electrically connect the conductive housing 430 and the biometric circuit board 420 contacts the biometric circuit board 420; a second connection point (e.g., the second connection point 422 of FIG. 4), which is a point at which a second conductive connection member configured to electrically connect a biometric button (e.g., the biosignal key button 432 of FIG. 4) and the biometric circuit board 420 contacts the biometric circuit board 420; and a third connection point (e.g., the third connection point 423 of FIG. 4), which is a point at which a third conductive connection member configured to electrically connect the main circuit board 410 and the biometric circuit board 420 contacts the biometric circuit board 420, wherein the conductive housing 430 may include a first shorting point physically/electrically (or operatively) connected to the biometric circuit board 420 and the main circuit board 410 to form an antenna path.

According to one or more embodiments, the biometric key button 432 may be positioned at a surface of the conductive housing 430 and be electrically isolated from the conductive housing 430.

According to one or more embodiments, the first shorting point (e.g., the first shorting point 431 of FIG. 4) may be positioned at the conductive housing and be connected to the first connection point through a first conductive connection member.

According to one or more embodiments, the biometric circuit board may be connected to the biometric button of the conductive housing to transmit and/or receive biometric information and biometric button signals.

According to one or more embodiments, the biometric circuit board may further include a first capacitor (e.g., the first capacitor 426 of FIG. 4) configured to block biosignal interference between the first connection point and the third connection point.

According to one or more embodiments, the biometric circuit board may further include a first inductor (e.g., the first inductor 428 of FIG. 4) configured to block RF signal interference between the second connection point and the third connection point.

According to one or more embodiments, the main circuit board may include an antenna circuit for transmitting and/or receiving RF signals, a biometric sensor configured to transmit and/or receive biosignals, and a fourth connection point (e.g., the fourth connection point 414 of FIG. 4). The fourth connection point 414 may exist at the main circuit board, be connected to the third connection point through a third conductive connection member, and be positioned between the antenna circuit and the biometric sensor.

According to one or more embodiments, the main circuit board may further include a second capacitor (e.g., the second capacitor 416 of FIG. 4) configured to block biosignal interference between the fourth connection point and the antenna circuit.

According to one or more embodiments, the main circuit board may further include a second inductor (e.g., the second inductor 418 of FIG. 4) configured to block RF signal interference between the fourth connection point and the biometric sensor.

According to one or more embodiments, the biometric circuit board may include a flexible printed circuit board (FPCB), and the conductive connection member may include a c-clip.

According to one or more embodiments, the electronic device may further include a feeding point (e.g., the feeding point 440 of FIG. 4) and a second shorting point (e.g., the second shorting point 442 of FIG. 4) generated through a contact between the conductive housing and the main circuit board, and a processor. The processor may control whether an antenna is used and whether an RF signal is transmitted and/or received.

According to one or more embodiments, in the antenna, as a distance between the feeding point and the shorting point decreases, a high resonant frequency may move to a higher band, and as a distance between the feeding point and the shorting point increases, a low resonant frequency may move to a lower band.

According to one or more embodiments, the electronic device may further include a first switch (e.g., the first switch 411a of FIG. 10), and the first switch may be switched to connect the feeding point and the first shorting point or may be switched to connect the feeding point and the second shorting point. The processor may control feeding path switching of the first switch.

According to one or more embodiments, in the case that the feeding point and the first shorting point are switched to be connected, a first resonant frequency of the antenna may be determined based on the distance between the feeding point and the first shorting point, in the case that the feeding point and the second shorting point are switched to be connected, a second resonant frequency of the antenna may be determined based on the distance between the feeding point and the second shorting point.

According to one or more embodiments, the electronic device may further include a processor, a biometric sensor, a first switch, and a biological switch (e.g., the biological switch 412a of FIG. 10). The processor may control transmission and/or reception of an RF signal through the first switch connected to the antenna circuit, and the biometric sensor may control transmission and/or reception of a biosignal through a bioswitch connected thereto.

What is claimed is:

1. An electronic device comprising:
   a conductive housing;
   a main circuit board; and
   a biometric circuit board configured to measure body information,
   wherein the biometric circuit board comprises:
      a first connection point at which a first conductive connection member contacts the biometric circuit board, the first conductive connection member being configured to electrically connect the conductive housing and the biometric circuit board;

a second connection point at which a second conductive connection member contacts the biometric circuit board, the second conductive connection member being configured to electrically connect a biometric button and the biometric circuit board; and a third connection point at which a third conductive connection member contacts the biometric circuit board, the third conductive connection member being configured to electrically connect the main circuit board and the biometric circuit board, and wherein the conductive housing comprises a first shorting point electrically connected to the biometric circuit board and the main circuit board to provide an antenna path.

2. The electronic device of claim 1, wherein the biometric button is provided at a surface of the conductive housing and electrically isolated from the conductive housing.

3. The electronic device of claim 1, wherein the first shorting point is provided at the conductive housing and the first shorting point is connected to the first connection point through the first conductive connection member.

4. The electronic device of claim 1, wherein the biometric circuit board is connected to the biometric button of the conductive housing to transmit or receive biometric information and biometric button signals.

5. The electronic device of claim 1, wherein the biometric circuit board further comprises a first capacitor configured to block biosignal interference between the first connection point and the third connection point.

6. The electronic device of claim 1, wherein the biometric circuit board further comprises a first inductor configured to block radio frequency (RF) signal interference between the second connection point and the third connection point.

7. The electronic device of claim 1, wherein the main circuit board comprises:
an antenna circuit configured to transmit or receive a radio frequency (RF) signal;
a biometric sensor configured to transmit or receive a biosignal; and
a fourth connection point connected to the third connection point through the third conductive connection member, and provided between the antenna circuit and the biometric sensor.

8. The electronic device of claim 7, wherein the main circuit board further comprises a second capacitor configured to block biosignal interference between the fourth connection point and the antenna circuit.

9. The electronic device of claim 7, wherein the main circuit board further comprises a second inductor configured to block RF signal interference between the fourth connection point and the biometric sensor.

10. The electronic device of claim 1, wherein the biometric circuit board comprises a flexible printed circuit board, and
wherein each of the first, second, and third conductive connection members comprises a c-clip.

11. The electronic device of claim 1, further comprising:
a feeding point;
a second shorting point generated through a contact between the conductive housing and the main circuit board; and
a processor configured to control whether an antenna is used and whether a radio frequency (RF) signal is transmitted or received.

12. The electronic device of claim 11, wherein, in the antenna, a high resonant frequency moves to a high band as a distance between the feeding point and the second shorting point decreases, and a low resonant frequency moves to a lower band as a distance between the feeding point and the second shorting point increases.

13. The electronic device of claim 11, further comprising a first switch,
wherein the first switch is switched to connect the feeding point and the first shorting point or the first switch is switched to connect the feeding point and the second shorting point, and
wherein the processor is further configured to control a switching of a path of the RF signal of the first switch.

14. The electronic device of claim 13, wherein, based on the feeding point and the first shorting point that are switched to be connected, a first resonant frequency of the antenna is determined based on a distance between the feeding point and the first shorting point, and
wherein, based on the feeding point and the second shorting point that are switched to be connected, a second resonant frequency of the antenna is determined based on a distance between the feeding point and the second shorting point.

15. The electronic device of claim 1, further comprising:
a processor;
an antenna circuit;
a biometric sensor;
a first switch; and
a bioswitch,
wherein the processor is configured to control a transmission or a reception of a radio frequency (RF) signal through the first switch connected to the antenna circuit, and
wherein the biometric sensor is configured to control a transmission or a reception of a biosignal through the bioswitch.

* * * * *